United States Patent
Zimmermann et al.

(10) Patent No.: US 7,379,832 B2
(45) Date of Patent: May 27, 2008

(54) MULTI-CHANNEL METERING APPARATUS WITH AUTOMATIC CALIBRATION

(75) Inventors: Peter Zimmermann, Kahla (DE);
Torsten Rausch, Jena (DE); Gerd Heibe, Jena (DE); Hartmut Köberich, Kahla (DE); Simon Renard, Jena (DE); Thomas Moore, Drackendorf (DE); Wolfgang Krämer, Jena (DE)

(73) Assignee: CyBio AG, Jena (DE)

( * ) Notice: Subject to any disclaimer, the term of this patent is extended or adjusted under 35 U.S.C. 154(b) by 572 days.

(21) Appl. No.: 10/722,366

(22) Filed: Nov. 25, 2003

(65) Prior Publication Data
US 2004/0232162 A1 Nov. 25, 2004

(30) Foreign Application Priority Data
Nov. 26, 2002 (DE) ................................ 102 55 595

(51) Int. Cl.
*G06F 19/00* (2006.01)
(52) U.S. Cl. ........................................ 702/100; 702/55
(58) Field of Classification Search ................. 702/85, 702/100, 55; 73/1.34, 1.36, 1.74, 863.31, 73/863.32, 863.33
See application file for complete search history.

(56) References Cited

U.S. PATENT DOCUMENTS

| | | | |
|---|---|---|---|
| 5,441,204 A | 8/1995 | Tappel et al. | |
| 5,741,554 A | 4/1998 | Tisone | |
| 5,743,960 A | 4/1998 | Tisone | |
| 5,916,524 A | 6/1999 | Tisone | |
| 6,063,339 A | 5/2000 | Tisone et al. | |
| 6,112,605 A * | 9/2000 | Papen et al. | 73/864.22 |
| 6,422,431 B2 * | 7/2002 | Pelc et al. | 222/422 |
| 6,576,295 B2 | 6/2003 | Tisone | |
| RE38,281 E | 10/2003 | Tisone | |
| 6,983,636 B2 * | 1/2006 | Johnson et al. | 73/1.36 |
| 2002/0001675 A1 | 1/2002 | Tisone | |

(Continued)

FOREIGN PATENT DOCUMENTS

EP 0 810 438 12/1997

(Continued)

OTHER PUBLICATIONS

European Search Report for European Patent Application Serial No. EP 03 02 7084, dated Jul. 15, 2005, 3 pgs.

Primary Examiner—John Barlow
Assistant Examiner—Douglas N Washburn
(74) Attorney, Agent, or Firm—Reed Smith LLP

(57) ABSTRACT

Multi-channel metering apparatus with automatic calibration, where the individual dispensing channels 1, the micro-valves 4 of which are connected with the outlets of a distributor 8, 13 or 15 whose inlet is filled with fluid by a vessel 9, 14 or 17 thus connected, are able to be calibrated in relation to each other in that between the vessel 9, 14 or 17 and the inlet of the distributor 8, 13 or 15 a flow sensor 10 is arranged which for calibration during delivery of the fluid via a respective nozzle 2 of a respective dispensing channel 1 records the flow and generates signals which are respectively assigned to a defined opening time of a micro-valve 4 and a specific dispensing channel 1 and thus stored allows for individual control of the micro-valves 4 in order to equalize the tolerances of the dispensing channels 1.

4 Claims, 3 Drawing Sheets

U.S. PATENT DOCUMENTS

Figure 1:
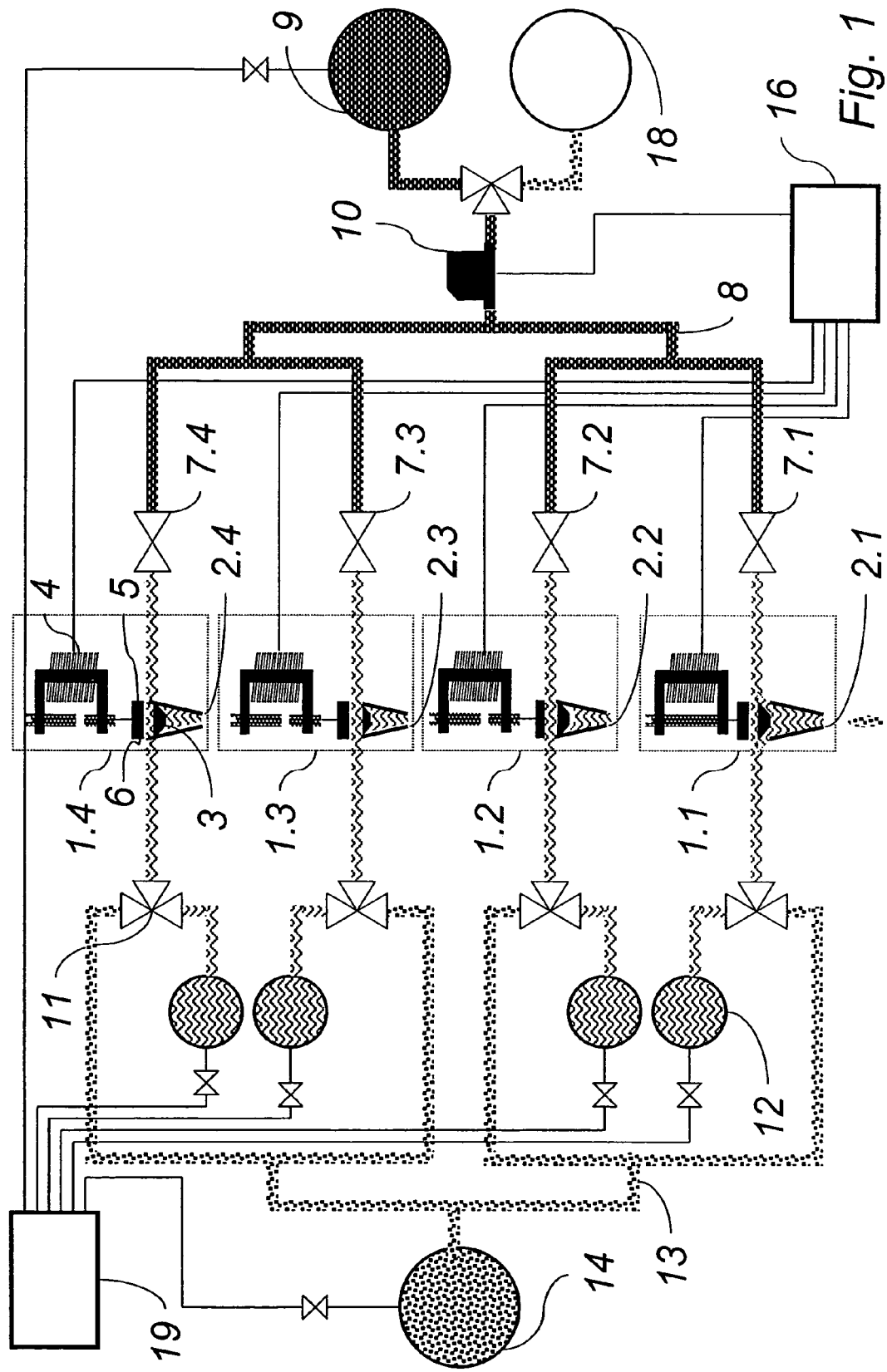

| | | |
|---|---|---|
| 2002/0064482 A1 | 5/2002 | Tisone et al. |
| 2002/0159919 A1 | 10/2002 | Churchill et al. |
| 2003/0003027 A1 | 1/2003 | Albert et al. ............... 422/100 |
| 2003/0175163 A1* | 9/2003 | Shvets et al. ............... 422/100 |
| 2004/0020938 A1 | 2/2004 | Boillat et al. |

FOREIGN PATENT DOCUMENTS

| | | |
|---|---|---|
| EP | 1 036 594 | 9/2000 |
| EP | 1 036 594 A2 | 9/2000 |
| EP | 1 099 480 A2 | 5/2001 |
| EP | 1099480 | 5/2001 |
| JP | 2000-258438 | 9/2000 |
| WO | WO 00/01798 | 1/2000 |
| WO | WO 02/33423 | 4/2002 |

\* cited by examiner

MULTI-CHANNEL METERING APPARATUS WITH AUTOMATIC CALIBRATION

The invention involves a multi-channel metering apparatus as it is generically known from WO 02/33423.

For multi-channel metering apparatuses which are primarily employed today in fully automatic laboratory equipment in pharmacological, molecular-biological, biochemical and chemical research, the constant task in principle is to deliver numerous tiny volumes (tests) of fluid reagents (dispensing fluid) precisely proportioned onto a carrier, e.g. a micro titration plate, in the shortest possible time in both localized and quantitative terms. The quantitatively precise dosage correspondingly represents an essential performance feature for multi-channel metering apparatuses. Thus a small fluctuation range when it comes to the respective volumes over all of the dispensing channels in parallel operation is often of greater value than the volume fluctuation range over an individual dispensing channel in serial operation. In order to obtain a small volume fluctuation range and thus a small coefficient of variation different measures are taken for generically similar devices from the state of the art.

In contrast to comparable devices for printing, multi-channel metering apparatuses are also supposed to be suitable for dispensing fluids of different physical properties, such as viscosity or to provide samples from tests of different dispensing fluids and/or volumes.

Generically similar metering apparatuses differ, among other things, in the way in which the dispensing fluid reaches the respective discharge opening of a dispensing channel (tip and/or nozzle) and the technical means with which proportioned delivery is effected.

With regard to accommodation of the dispensing fluid, known devices are divided into those where the dispensing fluid is suctioned in (pick up dispenser) via the discharge opening (from the front) and those with which the dispensing fluid is conveyed to the discharge opening from the rear (bulk reagent dispenser). For the purpose of differentiation the discharge opening in the case of pick up dispensers shall be designated as the tip and nozzle in the case of bulk reagent dispensers.

If one divides the known devices according to the means with which a proportioned delivery is effected, then there should first be a fundamental differentiation made between technical solutions where delivery can only be controlled over all tips/nozzles (manifold systems) and those with which the delivery of each individual tip/nozzle may be controlled (multi-single-channel systems).

In order to be able to simultaneously deliver a uniform volume over all nozzles with a manifold system, different distributor structures are known in particular from the state of the art with which the dispensing fluid is supposed to be evenly distributed to the nozzles from a common storage vessel. Such distributor structures are disclosed for example in U.S. Pat. No. 5,441,204 and in EP 1 036 594. Even delivery of the drops is realized in U.S. Pat. No. 5,441,204 through an electrostatic principle in that the continuously conveyed fluid is electro-statically charged and released from the surface of the tip by an electrical field. In EP 1 036 594 the fluid is carried at a high speed to the discharge openings via a flexible connection and a distributor. With an abrupt stop of the fluid flow which briefly exists due to the inertia, thus providing for contraction of the flexible connection, the jet breaks off due to the high kinetic energy without forming a drop. Fluid remainders are withdrawn from the discharge openings with easing of the connection.

These technical solutions necessarily presuppose that all of the nozzles are fed from a common storage vessel, whereby only the same dispensing fluid may be delivered over all of the nozzles. Thus there is no possibility of providing a test sample of different dispensing fluids and no differentiation may be made in the delivery quantity of the nozzles among themselves.

In patent application WO 00/01798 a multi-channel metering apparatus is described with which all of the nozzles can be filled from both a common and from different storage vessels and with which different volumes can also be delivered.

The individual nozzles respectively form independent dispensing channels in relation to each other with a syringe pump, a flexible connection and a valve. An additional volume which expands and thus effects overpressure in the connection closed at the other end by means of the valve is introduced into the flexible connection filled with dispensing fluid via the defined stroke of the syringe pump. Precisely this additional volume is delivered with opening of the valve.

A metering apparatus with a pressure pump and a conventional valve is described in U.S. Pat. No. 5,741,554. The pressure pump, a syringe pump filled with dispensing fluid, is connected with a hose at the other end of which a solenoid valve is arranged near the nozzle. The motor-driven piston of the syringe pump is powered with a defined speed which determines the flow rate. Together with the frequency of the valve it determines the dispensed volume. If, for example, the pump produces a flow rate of 1 ml/s and the frequency of the opening/closing cycle of the valve amounts to 100 per second, then the droplet size is 10 nl.

The basic principles described for dosage of the dispensing volume, namely via path (stroke of the syringe pump) and/or a time (opening time of the valve) can be verified with numerous further descriptions.

With all of these technical solutions it is a constant task to keep the coefficient of variation (CV) (deviation of the individual dispensing volumes from their average value) in serial operation of the individual dispenser (dispensing channel) as small as possible. Coefficients of variation of less than 2% with a delivery volume of 500 nl and less than 5% with 50 nl are typical. As a rule, manufacturers do not indicate a coefficient of variation based on the average value of all of the individual dispensers (dispensing channels) of a multi-channel metering apparatus in parallel operation. This will already be substantially larger due to the mechanical tolerances of the dispensing channels in relation to each other alone.

Presumably there is the widest possible adjustment of the dispensing channels (channel alignment) to each other in the state of the art only through targeted selection of the components during assembly of the modules. It is also conceivable that the delivery volume of the individual tips/nozzles of the individual dispensing channels is measured with external means of measurement and different control signals are formed for the individual dispensing channels from the different measurement results in order to adjust tolerances in the delivery volume with the same stroke of the individual syringe pumps and/or the same opening time of the individual valves by an individual stroke and/or an individual opening time. Such a calibration presupposes the presence of suitable measuring instruments and cannot be carried out so easily on a multi-channel metering apparatus which is integrated into laboratory equipment.

In patent application WO 02/33423 a dispensing apparatus is described with which the dispensing volume of each dispensing channel is respectively regulated via the opening time of the pertinent valve. In the individual dispensing channels means are provided for measuring the volume flow rate (flow sensors) as well as electronic means which control the valve in reaction to the measured values of the flow sensors. An 8-channel dispensing apparatus, offered by the patent applicant, which is based on the technical solution protected here promises a coefficient of variation CV of less than 5% (based on the average value over all of the dispensing channels) for a delivery volume in the range of 50 nl-10 µµl.

An advantage in contrast to the other indicated solutions is that the dispensing volume of all of the dispensing channels is not determined by controlling a specific time or path, but rather the volume flow rate serves as a controlled variable for the opening times of the respective individually assigned valve, so that calibration of the dispensing channels to the volume flow rate then becomes possible. Any tolerances capable of having an impact on the dosing volume up to the flow sensor do not influence the coefficient of variation. However, the tolerances of the flow sensors are directly accounted for by the controlled variable.

A further disadvantage consists in the compelling necessity for the high number of flow sensors which are required in the same quantity as the device has dispensing channels. Understandably for the expert the flow sensors must have a very short reactivity in order to achieve a delivery volume that is as precise as possible. Such flow sensors are technologically complex and not very durable.

It is the object of the invention to create a multi-channel metering apparatus which allows for more precise automatic calibration of the individual dispensing channels in relation to each other.

This task is solved according to the invention with the characteristics of claim 1.

Advantageous embodiments are described in the dependant claims.

It is essential for the invention that in an apparatus in accordance with a multi-single-channel system that a flow sensor is integrated and between the flow sensor and each nozzle paths of the same fluid resistance are present. Measurement of the absolute volume flow rate, for which a flow sensor is usually used, is not the actual objective here, but only the means for the purpose of the calibration. The particular advantage of the invention consists in the fact that the coefficient of variation (CV) can be substantially improved over all of the dispensing channels for multi-channel metering apparatuses with time-controlled micro-valves insofar as the effect of the main factors of influence which results in a different delivery volume of the individual dispensing channels is solved in terms of control technology. The main factors of influence are the mechanical tolerances of the individual connections to the nozzles, including the valves and nozzles (local tolerances) as well as possible temporal changes, e.g. through deposits on the nozzles or change of the nozzles, changes of temperature and aging of the fluids which lead to a change in the viscosity (temporal tolerances). For the purpose of the calibration the micro-valves of the individual dispensing channels are opened successively for a defined period of time. The respective volume flow rate recorded by the flow sensor per opening time generates a signal which is stored assigned to a dispensing channel with the associated micro-valve and an opening time. In order to increase the accuracy the same micro-valve can also be opened repeatedly for the same time in succession and the corresponding signals integrated and be respectively stored assigned as an integration signal. Measured curves for the individual dispensing channels are formed by interpolation from the memory values which can be respectively assigned to a dispensing channel and different opening times. With the help of the measuring curves an opening time for an individual dispensing channel can then be assigned to each practically meaningful delivery volume. This measured variable processing up to delivery of the control signals to the micro-valves takes place in a control unit. The calibration can be repeated any number of times between the dispensing operations in order to correct the measuring curves. Through the integration of only one flow sensor a multi-channel metering apparatus can be created with little technical and material and expenditure which is capable of automatic calibration.

With the flow sensor arranged according to the invention not only can calibration of the dispensing channels be carried out, but blockage of the nozzles can also be monitored (anti-clogging check). To this end, as in the case of calibration, proportional measured values for the individual dispensing channels are formed for the volume throughput and compared with previously acquired measured values for free, unclogged nozzles. The degree of blockage of the nozzles of the individual dispensing channels can then be derived from the comparison.

In the following the invention shall be described in greater detail on the basis of drawings of three embodiments. For this purpose it shall be shown as follows:

FIG. 1: Basic diagram for a first embodiment where a flow sensor is arranged in a calibration medium path, FIG. 2: Basic diagram for a second embodiment where a flow sensor is arranged in a rinsing agent path, FIG. 3: Basic diagram for a third embodiment where a flow sensor is arranged in a dosing medium path.

In FIG. 1 a principle sketch is represented for a first embodiment of a multi-channel metering apparatus according to the invention, functioning in accordance with the principle of a bulk reagent dispenser with four dispensing channels 1 (1.1 to 1.4). In practical terms such a device is normally implemented with eight or a multiple of eight dispensing channels 1, whereby a device according to the invention is equally advantageous independent of the number of dispensing channels 1. A dispensing channel 1 respectively consists of a nozzle 2 (2.1 to 2.4), which is respectively connected with a discharge opening 3 of a micro-valve 4.

The respective micro-valves 4 have a first supply opening 5, each of which is respectively connected with the respective outlet of a calibration medium distributor 8 via a gate valve 7 (7.1-7.4). The calibration medium distributor 8 is constructed in such a way that the calibration fluid supplied via its only inlet is evenly distributed to the dispensing channels 1. That is, the paths between the inlet and the outlets of the calibration medium distributor 8 are identical and thus have the same fluidic resistance. A flow sensor 10 is arranged in the path between the inlet of the calibration medium distributor 8 and an upstream calibration medium vessel 9. The calibration medium distributor 8 may be occasionally connected with a rinsing agent collector 18 for rinsing the device.

A respective second supply opening 6 of each micro-valve 4 is connected by a valve 11 alternatively with a respective dispensing medium vessel 12 and/or one of the outlets of a rinsing agent distributor 13. The rinsing agent distributor 13 is conceived in such a way that it evenly distributes the purging fluid, which is supplied to it by way of its only inlet from a rinsing agent vessel 14, to the dispensing channels 1. The supply openings 5, 6 can also alternately serve to remove the interspersing fluid with the micro-valve 4 closed. Thus the dispensing fluid can also be pressed beyond the micro-valves 4 to the calibration medium distributor 8. The resultant advantages for the calibration shall be described later. A micro-valve suitable for the device is described in EP 1099480.

The complete device represents a closed pressure tight system with the closed micro-valves 4. All of the connections between the vessels 9, 12, 14 and the discharge openings 3 of the micro-valves 4 are air-free and filled with one of the fluids. By supplying compressed air or a pressurized gas by means of a pressure source 19 (e.g. electronically regulated pump, compressed-air bottle, inert gas bottle) alternatively into the calibration medium container 9, the dispensing medium vessel 12 or the rinsing agent vessel 14 and correlating switching of the valves 11, the gate valves 7 and the micro-valves 4 to this end, dispensing can be effected via the nozzles 2.

A characteristic of the device which is essential for the invention is the integration of a flow sensor 10 for automatic calibration of the dispensing channels 1 in relation to each other. In the first shown embodiment, as previously mentioned, the flow sensor 10 should be arranged directly at the inlet of the calibration medium distributor 8. As a rule calibration with the calibration fluid or with the dispensing fluid is advantageous. Calibration with the purging fluid is also possible theoretically, but with this first embodiment there are no advantages in relation to the other two possibilities.

For calibration of the dispensing channels 1 with calibration fluid the two fluid columns, on the one hand the calibration fluid and on the other hand the dispensing fluid or the purging fluid, from the viewpoint of the flow sensor 10 must meet behind the micro-valves 4, i.e. the calibration fluid is queued at the respective two supply openings 5, 6 of the micro-valves 4. (in FIG. 1 the dispensing fluid stands here). Now, for example, if for calibration of the first dispensing channel 1.1 the first gate valve 7.1 is opened while the other gate valves 7.2 to 7.4 are closed and compressed air is introduced into the calibration medium vessel 9, then the calibration fluid is delivered by the first nozzle 2.1 as long as the first micro-valve is 4 is opened. The nozzle 2.1 is now opened successively for different periods of time. The other nozzles 2.2-2.4 are then sequentially opened in accordance with the same defined period of time. The respective volume flow rate recorded by the flow sensor 10 per opening time generates a signal which is assigned to and stored for a micro-valve 4 and an opening time respectively. By interpolation of the measured values (signals) a measuring curve can be provided for each dispensing channel 1 by means of which a volume flow rate can be individually assigned to each opening time for the respective dispensing channel 1. Tolerances of the individual dispensing channels 1 relative to each other result in the fact that the flow sensor 10 measures the same volume flow rate for the individual dispensing channels 1 according to different lengths of time, thus creating different measuring curves. Accordingly the individual valves 11 are opened for different periods of time in order to deliver the same volume during the dispensing operation. Thus local tolerances are excluded in their impact on the coefficient of variation of the dispensing channels in relation to each other. Calibration of the flow sensor 10 is not required since calibration for all of the dispensing channels 1 takes place with the same flow sensor 10. Calibration with a calibration fluid has the advantage that no valuable dispensing fluid is lost. It is, however, clear to the expert that this calibration can really only exclude the local tolerances if the dispensing fluid in its physical characteristics, in particular the viscosity, virtually corresponds to the calibration fluid.

As already mentioned, calibration of a device in accordance with the first embodiment can also take place with the dispensing fluid (represented in FIG. 1). For this purpose the fluid columns of the calibration fluid and the dispensing fluid from the viewpoint of the flow sensor 10 must meet before the micro-valves 4, i.e. the dispensing fluid is available at the two respective supply openings 5, 6 of the micro-valves 4. Thus the available volume of the dispensing fluid at the supply openings 5 must be greater than the volume which is discharged through the respective micro-valves 4 for calibration. Now, for example, if for calibration of the first dispensing channel 1.1 the first gate valve 7.1 is opened while the other gate valves 7.2 to 7.4 are closed and compressed air is introduced into the calibration medium vessel 9, then the calibration fluid is forced back and delivered through the first nozzle 2.1 as long as the first micro-valve is 4 is opened.

If one assumes that the dispensing fluid has a higher viscosity than the calibration fluid, then the velocity of flow will be lower with equal pressure and thus the opening time of the micro-valve 4.1 longer for the same delivery volume. The individual dispensing channels 1 can thus be calibrated for different dispensing fluids, but also for the same dispensing fluid without the flow sensor 10 coming into contact with the dispensing fluid.

Figure 2:
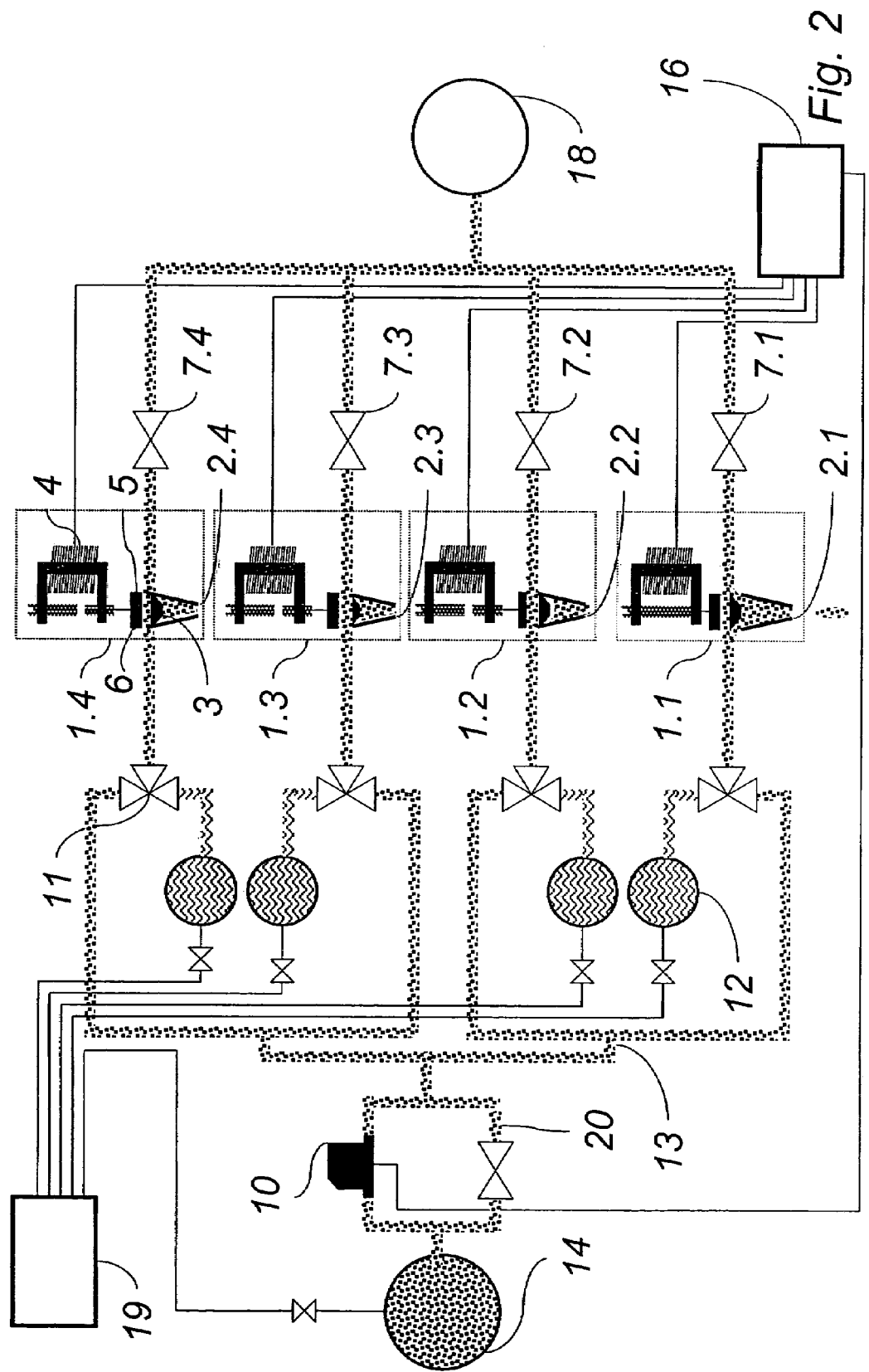

A second embodiment, represented in FIG. 2, is to essentially differ from the first embodiment in that the flow sensor 10 is arranged at the entrance of the rinsing agent distributor 13. The device then does not require the calibration medium supply. In principle no micro-valve 4 with two inlet openings 5, 6 is also required. However, its employment represents an advantage for the aeration alone. As already described, calibration is successively effected for the individual dispensing channels 1 in that the purging fluid is delivered via the points 2. In comparison to calibration with a calibration fluid the disadvantage here consists in the fact that calibration takes place with a fluid which can have completely different physical characteristics than the dispensing fluid. However, the expenditure for a device in accordance with the second embodiment is clearly lower than for one in accordance with the first embodiment.

Since the sensitivity of the flow sensor 10 increases with the flow velocity, reduction of the path cross section in the area of the flow sensor 10 represents an advantage. Nevertheless, in order to make it possible to put greater volumes of purging fluid through the dispensing channels 1, the path cross section must be large precisely at the entrance of the rinsing agent distributor 13. Thus by way of advantage the path is divided into a path of small cross section in which the flow sensor 10 is introduced and a parallel running path of large cross section, the bypass 20.

Figure 3:
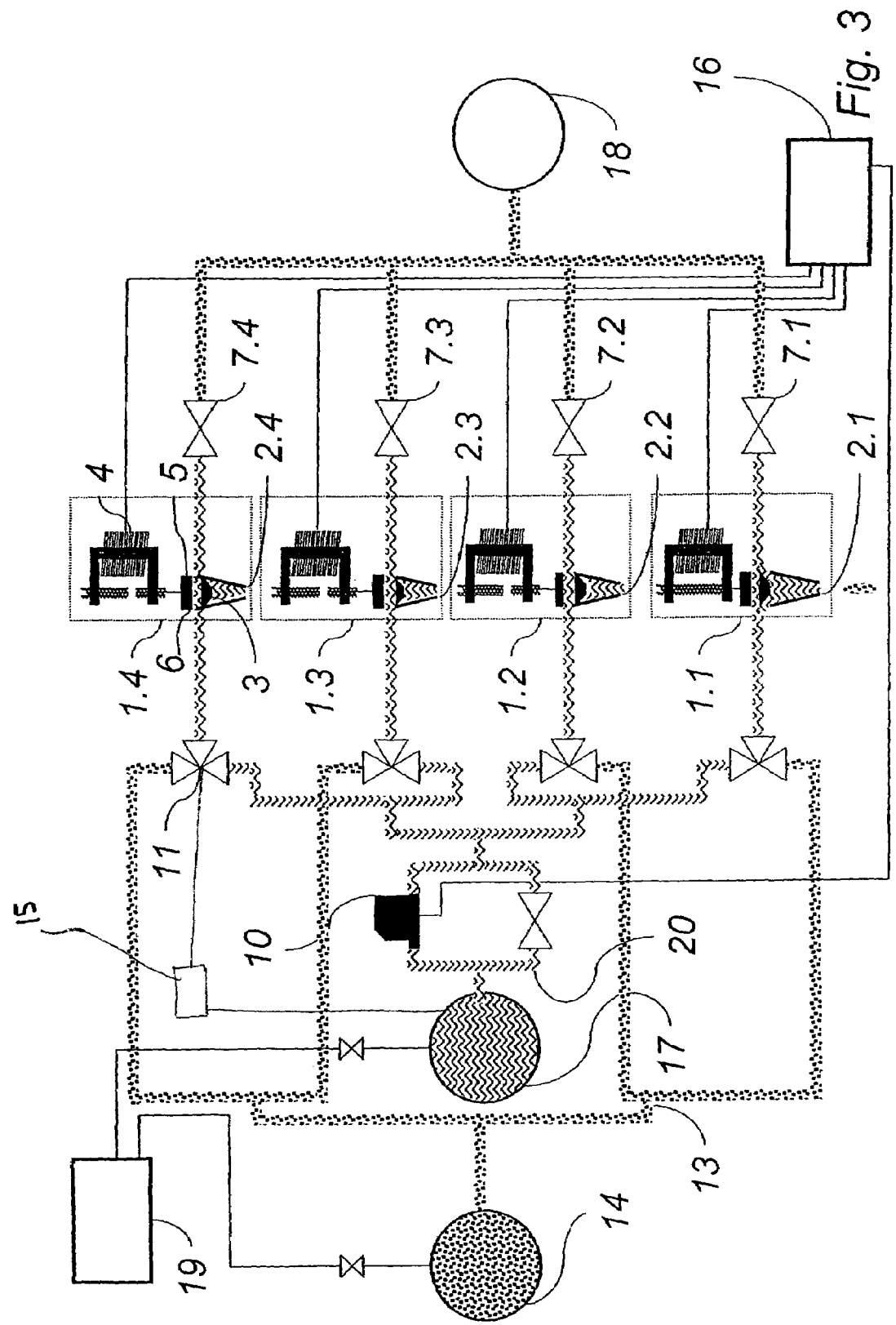

In a third embodiment, represented in FIG. 3, each dispensing channel 1 is not assigned its own dispensing medium vessel 12 compared with the second embodiment, but rather all dispensing channels 1 are supposed to be supplied from a common dispensing medium vessel 17. Instead of the alternative individual dispensing medium vessel 12 or a common dispensing medium vessel 17, the device can of course be equipped with both supply variants. In the case of a common dispensing vessel 17, a dispensing medium distributor 15 is required for the dispensing fluid by way of analogy to the rinsing agent distributor 13. The flow sensor 10 should be located accordingly at the entrance of the dispensing medium distributor 15.

In principle a respective flow sensor 10 could be introduced for each dispensing channel 1, near to the supply openings 5 or 6. However, the advantage presented by possible simultaneous calibration does not outweigh the disadvantages of extra costs and the additional calibration expenditure for the flow sensors 10 in relation to each other.

With the introduction of a flow sensor 10 into a multi-channel metering apparatus the possibility of one-time calibration of the apparatus is created without an external means of calibration prior to commissioning or any number of times, e.g. after replacement of micro-valves 4 or nozzles 2 or for employment of other dispensing fluids as well as breaks in the process between dispensing of two micro titration plates to and/or monitoring blockage of the nozzles.

LIST OF THE REFERENCE SYMBOLS USED

1 Dispensing channel
2 Nozzle
3 Discharge opening
4 Micro-valve
5 First supply opening
6 Second supply opening
7 Gate valve
8 Calibration medium distributor
9 Calibration medium vessel
10 Flow sensor
11 Valve
12 Dispensing medium vessel
13 Rinsing agent distributor
14 Rinsing agent vessel
15 Dispensing medium distributor
16 Control unit
17 Common dispensing medium vessel
18 Rinsing agent collector
19 Pressure source
20 Bypass

The invention claimed is:

1. Multi-channel metering apparatus with automatic calibration with several dispensing channels (1) respectively with a nozzle (2) and a micro-valve (4), whereby a plurality of micro-valves (4) each exhibit a discharge opening (3), which is respectively connected with one of a plurality of nozzles (2) and at least one supply opening (5 or 6) is respectively present on the micro-valves (4), which are respectively connected with an outlet of a distributor (8,13 or 15), the inlet of which is indirectly connected via a flow sensor (10) with a vessel (9, 14 or 17) filled with a fluid and paths between the inlet and a plurality of outlets of the distributor exhibit the same fluidic resistance as well as a pressure source (19) to produce overpressure in the vessel (9, 14 or 17) and a control unit (16) connected with the flow sensor (10) and the micros-valves (4) and generates the individual control signals for the micro-valves (4) from the measured values received from the flow sensor (10).

2. Multi-channel metering apparatus in accordance with claim 1, characterized by, the fact that the supply openings (5 or 6) are first supply openings (5) and second supply openings (6), whereby the first supply openings (5) are respectively connected with an outlet of the distributor (8, 13 or 15), which here is a calibration medium distributor (8) filled with a calibration medium, and the second supply openings (6) which respectively exhibit a connection with a respective dispensing medium vessel (12) such that at the first supply openings (5) the calibration fluid and at the second supply openings (6) the dispensing fluid is available and on admission of the vessel (9, 14 or 17), which here is a calibration fluid is delivered, whereby dispensing channels are calibrated in relation to each other with the calibration fluid.

3. Multi-channel metering apparatus in accordance with claim 1, characterized by, the fact that the supply openings (5 or 6) are first supply openings (5) and second supply openings (6), whereby the first supply openings (5) are respectively connected with an outlet of the distributor (8, 13 or 15) which here is a calibration medium distributor (8) filled with a calibration medium, and the second supply openings (6) respectively exhibit a connection with a dispensing medium vessel (12) such that at the first supply openings (5) and at the second supply openings (6) the dispensing fluid is available and on admission of the vessel (9, 14 or 17), which here is a calibration medium vessel (9) with pressure via an opened micro-valve (4) dispensing fluid is delivered, whereby dispensing channels can be calibrated in relation to each other with different dispensing fluid.

4. Multi-channel metering apparatus in accordance with claim 1, characterized by, the fact that the distributor (8, 13 or 15) is a rinsing agent distributor (13) and the vessel (9, 14 or 17) is a rinsing agent vessel (14) and both are indirectly connected with each other, whereby in parallel to the flow through the flow sensor (10) a bypass (20) is present which allows for a high throughput volume of purging fluid.

* * * * *